United States Patent
Wilson et al.

(10) Patent No.: US 11,457,855 B2
(45) Date of Patent: Oct. 4, 2022

(54) METHOD AND SYSTEM FOR UTILIZING EMPIRICAL NULL HYPOTHESIS FOR A BIOLOGICAL TIME SERIES

(71) Applicant: Persyst Development Corporation, Solana Beach, CA (US)

(72) Inventors: Scott B. Wilson, Del Mar, CA (US); Mark L. Scheuer, Wexford, PA (US)

(73) Assignee: Persyst Development Corporation, Solana Beach, CA (US)

( * ) Notice: Subject to any disclaimer, the term of this patent is extended or adjusted under 35 U.S.C. 154(b) by 11 days.

(21) Appl. No.: 16/294,917

(22) Filed: Mar. 7, 2019

(65) Prior Publication Data
US 2019/0274566 A1     Sep. 12, 2019

Related U.S. Application Data

(60) Provisional application No. 62/641,947, filed on Mar. 12, 2018.

(51) Int. Cl.
*A61B 5/374*     (2021.01)
*A61B 5/00*     (2006.01)
*A61B 5/316*     (2021.01)

(52) U.S. Cl.
CPC .............. *A61B 5/374* (2021.01); *A61B 5/316* (2021.01); *A61B 5/7267* (2013.01)

(58) Field of Classification Search
CPC ... A61B 5/048; A61B 5/04014; A61B 5/7267; A61B 5/7264; A61B 5/7235; A61B 5/7246; A61B 5/7275; A61B 5/0476; A61B 5/04012; A61B 5/4064; A61B 5/04001; A61B 5/4094; A61B 5/04; G01R 23/00; G06N 7/005; G06N 5/04; G06F 17/15
See application file for complete search history.

(56) References Cited

U.S. PATENT DOCUMENTS

| | | |
|---|---|---|
| RE30,502 E | 2/1981 | Lencioni, Jr. |
| 4,550,736 A | 11/1985 | Broughton et al. |
| 4,644,956 A | 2/1987 | Morgenstern |
| 4,709,702 A | 12/1987 | Sherwin |
| 4,936,306 A | 6/1990 | Doty |
| 4,967,038 A | 10/1990 | Gevins et al. |

(Continued)

FOREIGN PATENT DOCUMENTS

WO     WO2000039337     7/2000

OTHER PUBLICATIONS

Singh, A. K., Asoh, H., Takeda, Y., & Phillips, S. (2015). Statistical detection of EEG synchrony using empirical bayesian inference. PloS one, 10(3), e0121795. (Year: 2015).*

(Continued)

*Primary Examiner* — Sean P Dougherty
*Assistant Examiner* — Jonathan E. Cooper
(74) *Attorney, Agent, or Firm* — Clause Eight; Michael Catania

(57) ABSTRACT

A method and system for utilizing empirical null hypothesis for a biological time series is disclosed herein. The method also includes calculating an amount that a second plurality of epochs is similar to a first plurality of epochs using large-scale testing to estimate an empirical null hypothesis for a subset of the epochs. The method also includes determining if the second plurality of epochs is from the same EEG recording.

2 Claims, 15 Drawing Sheets

(56) References Cited

U.S. PATENT DOCUMENTS

| | | | |
|---|---|---|---|
| 5,038,782 A | 8/1991 | Gevins et al. | |
| 5,230,344 A | 7/1993 | Ozdamar et al. | |
| 5,230,346 A | 7/1993 | Leuchter et al. | |
| 5,305,746 A | 4/1994 | Fendrock | |
| 5,309,909 A | 5/1994 | Gadsby et al. | |
| 5,626,145 A | 5/1997 | Clapp et al. | |
| 5,730,146 A | 3/1998 | Itil et al. | |
| 5,846,208 A | 12/1998 | Pichlmayr et al. | |
| 6,224,549 B1 | 5/2001 | Drongelen | |
| 6,334,856 B1 | 1/2002 | Allen et al. | |
| 6,493,576 B1 | 12/2002 | Dankwart-Eder | |
| 6,591,132 B2 | 7/2003 | Gotman et al. | |
| 6,658,287 B1 * | 12/2003 | Litt | A61B 5/374 600/544 |
| 6,735,467 B2 | 5/2004 | Wilson | |
| 6,931,274 B2 | 8/2005 | Williams | |
| 7,286,871 B2 | 10/2007 | Cohen | |
| 7,754,190 B2 | 7/2010 | Suffin | |
| 7,809,433 B2 | 10/2010 | Keenan | |
| 7,904,144 B2 | 3/2011 | Causevic et al. | |
| 7,941,201 B2 | 5/2011 | Chiou et al. | |
| 8,112,141 B2 | 2/2012 | Wilson et al. | |
| 8,155,736 B2 | 4/2012 | Sullivan et al. | |
| 8,185,183 B1 | 5/2012 | Wilson et al. | |
| 8,271,065 B1 | 9/2012 | Wilson et al. | |
| 8,428,681 B2 | 4/2013 | Wilson et al. | |
| 8,538,502 B1 | 9/2013 | Wilson et al. | |
| 8,666,484 B2 | 3/2014 | Nierenberg et al. | |
| 8,694,070 B2 | 4/2014 | Wilson | |
| 8,972,001 B2 | 3/2015 | Nierenberg et al. | |
| 9,055,927 B2 | 6/2015 | Wilson et al. | |
| 9,232,922 B2 | 1/2016 | Wilson et al. | |
| 10,022,291 B2 | 7/2018 | Wilson et al. | |
| 10,105,091 B2 | 10/2018 | Papay et al. | |
| 2002/0082551 A1 | 6/2002 | Ennen et al. | |
| 2002/0099306 A1 | 7/2002 | Shaw et al. | |
| 2003/0144601 A1 | 7/2003 | Prichep | |
| 2004/0059241 A1 | 3/2004 | Suffin | |
| 2004/0152957 A1 | 8/2004 | Stivoric et al. | |
| 2005/0059874 A1 | 3/2005 | Fuchs et al. | |
| 2005/0144042 A1 | 6/2005 | Joffe et al. | |
| 2006/0058606 A1 | 3/2006 | Davis et al. | |
| 2007/0135727 A1 | 6/2007 | Virtanen et al. | |
| 2007/0167858 A1 | 7/2007 | Virtanen et al. | |
| 2008/0027515 A1 | 1/2008 | Harris et al. | |
| 2008/0234973 A1 | 9/2008 | Ali | |
| 2008/0262335 A1 | 10/2008 | Sun et al. | |
| 2009/0062680 A1 | 3/2009 | Sandford | |
| 2009/0247895 A1 | 10/2009 | Morikawa et al. | |
| 2010/0098289 A1 | 4/2010 | Tognoli et al. | |
| 2010/0168603 A1 * | 7/2010 | Himes | A61B 5/6846 600/544 |
| 2011/0015503 A1 | 1/2011 | Joffe et al. | |
| 2011/0178421 A1 | 7/2011 | Schultz | |
| 2011/0224569 A1 | 9/2011 | Isenhart et al. | |
| 2015/0112223 A1 | 4/2015 | Nierenberg et al. | |
| 2015/0313497 A1 * | 11/2015 | Chang | A61B 5/377 600/544 |
| 2015/0351654 A1 | 12/2015 | Kilsgaard et al. | |
| 2017/0061217 A1 | 3/2017 | Cha et al. | |

OTHER PUBLICATIONS

International Preliminary Report for PCT Application PCT/US2019/021684, dated Jun. 13, 2019.

International Search Report for PCT Application PCT/US2019/021684, dated Jun. 13, 2019.

* cited by examiner

METHOD AND SYSTEM FOR UTILIZING EMPIRICAL NULL HYPOTHESIS FOR A BIOLOGICAL TIME SERIES

CROSS REFERENCE TO RELATED APPLICATION

The Present Application claims priority to U.S. Provisional Patent Application No. 62/641,947, filed on Mar. 12, 2018, which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The present invention generally relates to a method and system for utilizing empirical null hypothesis for a biological time series.

Description of the Related Art

An electroencephalogram ("EEG") is a diagnostic tool that measures and records the electrical activity of a person's brain in order to evaluate cerebral functions. Multiple electrodes are attached to a person's head and connected to a machine by wires. The machine amplifies the signals and records the electrical activity of a person's brain. The electrical activity is produced by the summation of neural activity across a plurality of neurons. These neurons generate small electric voltage fields. The aggregate of these electric voltage fields create an electrical reading which electrodes on the person's head are able to detect and record. An EEG is a superposition of multiple simpler signals. In a normal adult, the amplitude of an EEG signal typically ranges from 1 micro-Volt to 100 micro-Volts, and the EEG signal is approximately 10 to 20 milli-Volts when measured with subdural electrodes. The monitoring of the amplitude and temporal dynamics of the electrical signals provides information about the underlying neural activity and medical conditions of the person.

An EEG is performed to: diagnose epilepsy; verify problems with loss of consciousness or dementia; verify brain activity for a person in a coma; study sleep disorders; monitor brain activity during surgery, and additional physical problems.

Multiple electrodes (typically 17-21, however there are standard positions for at least 70) are attached to a person's head during an EEG. The electrodes are referenced by the position of the electrode in relation to a lobe or area of a person's brain. The references are as follows: F=frontal; Fp=frontopolar; T=temporal; C=central; P=parietal; O=occipital; and A=auricular (ear electrode). Numerals are used to further narrow the position and "z" points relate to electrode sites in the midline of a person's head. An electrocardiogram ("EKG") may also appear on an EEG display.

The EEG records brain waves from different amplifiers using various combinations of electrodes called montages. Montages are generally created to provide a clear picture of the spatial distribution of the EEG across the cortex. A montage is an electrical map obtained from a spatial array of recording electrodes and preferably refers to a particular combination of electrodes examined at a particular point in time.

In bipolar montages, consecutive pairs of electrodes are linked by connecting the the electrode input 2 of one channel to input 1 of the subsequent channel, so that adjacent channels have one electrode in common. The bipolar chains of electrodes may be connected going from front to back (longitudinal) or from left to right (transverse). In a bipolar montage signals between two active electrode sites are compared resulting in the difference in activity recorded.

Another type of montage is the referential montage or monopolar montage. In a referential montage, various electrodes are connected to input 1 of each amplifier and a reference electrode is connected to input 2 of each amplifier. In a reference montage, signals are collected at an active electrode site and compared to a common reference electrode.

Reference montages are good for determining the true amplitude and morphology of a waveform. For temporal electrodes, CZ is usually a good scalp reference.

Being able to locate the origin of electrical activity ("localization") is critical to being able to analyze the EEG. Localization of normal or abnormal brain waves in bipolar montages is usually accomplished by identifying "phase reversal," a deflection of the two channels within a chain pointing to opposite directions. In a referential montage, all channels may show deflections in the same direction. If the electrical activity at the active electrodes is positive when compared to the activity at the reference electrode, the deflection will be downward. Electrodes where the electrical activity is the same as at the reference electrode will not show any deflection. In general, the electrode with the largest upward deflection represents the maximum negative activity in a referential montage.

Some patterns indicate a tendency toward seizures in a person. A physician may refer to these waves as "epileptiform abnormalities" or "epilepsy waves." These include spikes, sharp waves, and spike-and-wave discharges. Spikes and sharp waves in a specific area of the brain, such as the left temporal lobe, indicate that partial seizures might possibly come from that area. Primary generalized epilepsy, on the other hand, is suggested by spike-and-wave discharges that are widely spread over both hemispheres of the brain, especially if they begin in both hemispheres at the same time.

There are several types of brain waves: alpha waves, beta waves, delta wave, theta waves and gamma waves. Alpha waves have a frequency of 8 to 12 Hertz ("Hz"). Alpha waves are normally found when a person is relaxed or in a waking state when a person's eyes are closed but the person is mentally alert.

Alpha waves cease when a person's eyes are open or the person is concentrating. Beta waves have a frequency of 13 Hz to 30 Hz. Beta waves are normally found when a person is alert, thinking, agitated, or has taken high doses of certain medicines. Delta waves have a frequency of less than 3 Hz. Delta waves are normally found only when a person is asleep (non-REM or dreamless sleep) or the person is a young child. Theta waves have a frequency of 4 Hz to 7 Hz. Theta waves are normally found only when the person is asleep (dream or REM sleep) or the person is a young child. Gamma waves have a frequency of 30 Hz to 100 Hz. Gamma waves are normally found during higher mental activity and motor functions.

General definitions for terms utilized in the pertinent art are set forth below.

Boolean algebra is the subarea of algebra in which the values of the variables are the truth values true and false, usually denoted 1 and 0 respnectively.

A Boolean network (BN) is a mathematical model of biological systems based on Boolean logic. The BN has a network structure consisting of nodes that correspond to genes or proteins. Each node in a BN takes a value of 1 or 0, meaning that the gene is or is not expressed.

Fuzzy logic is a form of many-valued logic; it deals with reasoning that is approximate rather than fixed and exact. Compared to traditional binary sets (where variables may take on true or false values) fuzzy logic variables may have a truth value that ranges in degree between 0 and 1. Fuzzy logic has been extended to handle the concept of partial truth, where the truth value may range between completely true and completely false. Furthermore, when linguistic variables are used, these degrees may be managed by specific functions. Irrationality can be described in terms of what is known as the "fuzzjective".

Multilayer perceptron ("MLP") is a feedforward artificial neural network model that maps sets of input data onto a set of appropriate outputs. An MLP consists of multiple layers of nodes in a directed graph, with each layer fully connected to the next one. Except for the input nodes, each node is a neuron (or processing element) with a nonlinear activation function.

Neural network ("NN") is an interconnected group of natural or artificial neurons that uses a mathematical or computational model for information processing based on a connectionist approach to computation. In more practical terms neural networks are non-linear statistical data modeling or decision making tools. They can be used to model complex relationships between inputs and outputs or to find patterns in data.

Perceptron is a simple model of an artificial neuron which can predict boolean events after having been trained on past events. The perceptron is specified by the number of inputs N, and the weights connecting the inputs to the output node. The weights are the parameters which must be either set by hand or learned by a learning algorithm.

ROC curve (receiver operating characteristic) is a graphical plot of test sensitivity as the y coordinate versus its 1 minus specificity or false positive rate (FPR), as the x coordinate. The ROC curve is an effective method of evaluating the performance of diagnostic tests.

"Amplitude" refers to the vertical distance measured from the trough to the maximal peak (negative or positive). It expresses information about the size of the neuron population and its activation synchrony during the component generation.

The term "analogue to digital conversion" refers to when an analogue signal is converted into a digital signal which can then be stored in a computer for further processing. Analogue signals are "real world" signals (e.g., physiological signals such as electroencephalogram, electrocardiogram or electrooculogram). In order for them to be stored and manipulated by a computer, these signals must be converted into a discrete digital form the computer can understand.

"Artifacts" are electrical signals detected along the scalp by an EEG, but that originate from non-cerebral origin. There are patient related artifacts (e.g., movement, sweating, ECG, eye movements) and technical artifacts (50/60 Hz artifact, cable movements, electrode paste-related).

The term "differential amplifier" refers to the key to electrophysiological equipment. It magnifies the difference between two inputs (one amplifier per pair of electrodes).

"Duration" is the time interval from the beginning of the voltage change to its return to the baseline. It is also a measurement of the synchronous activation of neurons involved in the component generation.

"Electrode" refers to a conductor used to establish electrical contact with a non-metallic part of a circuit. EEG electrodes are small metal discs usually made of stainless steel, tin, gold or silver covered with a silver chloride coating. They are placed on the scalp in special positions.

"Electrode gel" acts as a malleable extension of the electrode, so that the movement of the electrodes leads is less likely to produce artifacts. The gel maximizes skin contact and allows for a low-resistance recording through the skin.

The term "electrode positioning" (10/20 system) refers to the standardized placement of scalp electrodes for a classical EEG recording. The essence of this system is the distance in percentages of the 10/20 range between Nasion-Inion and fixed points. These points are marked as the Frontal pole (Fp), Central (C), Parietal (P), occipital (O), and Temporal (T). The midline electrodes are marked with a subscript z, which stands for zero. The odd numbers are used as subscript for points over the left hemisphere, and even numbers over the right.

"Electroencephalogram" or "EEG" refers to the tracing of brain waves, by recording the electrical activity of the brain from the scalp, made by an electroencephalograph.

"Electroencephalograph" refers to an apparatus for detecting and recording brain waves (also called encephalograph).

"Epileptiform" refers to resembling that of epilepsy <an epileptiform abnormality>.

"Filtering" refers to a process that removes unwanted frequencies from a signal.

"Filters" are devices that alter the frequency composition of the signal.

"Ideal frequency-selective filter" is a filter that exactly passes signals at one set of frequency and completely rejects the rest. There are three types of filter: "Low frequency" or in old terminology "high pass". Filters low frequencies. "High frequency" or in old terminology "low pass". Filters high frequencies. "Notch filter". Filters one frequency, usually 60 Hz. "Real filters" or "hardware filters" alter the frequency composition of the signal. After filtering the signal, the frequencies that have been filtered cannot be recovered. "Digital filters" change the frequency of the signal by performing calculations on the data.

"Frequency" refers to rhythmic repetitive activity (in Hz). The frequency of EEG activity can have different properties including: "Rhythmic". EEG activity consisting in waves of approximately constant frequency. "Arrhythmic". EEG activity in which no stable rhythms are present. "Dysrhythmic". Rhythms and/or patterns of EEG activity that characteristically appear in patient groups or rarely or seen in healthy subjects.

Hypothesis testing is the use of statistics to determine the probability that a given hypothesis is true.

"Montage" means the placement of the electrodes. The EEG can be monitored with either a bipolar montage or a referential one. Bipolar means that there are two electrodes per one channel, so there is a reference electrode for each channel. The referential montage means that there is a common reference electrode for all the channels.

"Morphology" refers to the shape of the waveform. The shape of a wave or an EEG pattern is determined by the frequencies that combine to make up the waveform and by their phase and voltage relationships. Wave patterns can be described as being: "Monomorphic". Distinct EEG activity appearing to be composed of one dominant activity. "Polymorphic". Distinct EEG activity composed of multiple frequencies that combine to form a complex waveform. "Sinusoidal". Waves resembling sine waves. Monomorphic activity usually is sinusoidal. "Transient". An isolated wave or pattern that is distinctly different from background activity.

"Spike" refers to a transient with a pointed peak and a duration from 20 to under 70 msec.

The term "sharp wave" refers to a transient with a pointed peak and duration of 70-200 msec.

The term "neural network algorithms" refers to algorithms that identify sharp transients that have a high probability of being epileptiform abnormalities.

"Noise" refers to any unwanted signal that modifies the desired signal. It can have multiple sources.

Null hypothesis is a hypothesis which is tested for possible rejection under the assumption that it is true (usually that the observations are the result of chance).

"Periodicity" refers to the distribution of patterns or elements in time (e.g., the appearance of a particular EEG activity at more or less regular intervals). The activity may be generalized, focal or lateralized.

Probability density P(x) of a continuous distribution is defined as the derivative of the distribution function D(x), where $$D'(x)=[P(x)]^X_{-\infty}=P(x)-P(-\infty)=P(x)$$

$$So\ D(x)=P(X\leq x)=\int_{-\infty}^{X} P(y)dy$$

"Sampling" or the term "sampling the signal" refers to reducing a continuous signal to a discrete signal. A digital signal is a sampled signal; obtained by sampling the analogue signal at discrete points in time.

The term "sampling interval" is the time between successive samples; these points are usually evenly spaced in time.

The term "sampling rate" refers to the frequency expressed in Hertz (Hz) at which the analogue-to-digital converter (ADC) samples the input analogue signal.

The term "Signal to Noise Ratio" (SNR) refers to a measurement of the amplitude of variance of the signal relative to the variance of the noise.

An EEG epoch is an amplitude of an EEG signal as a function of time and frequency.

An EEG recording has a tremendous amount of information, and it is difficult to determine if two sets of epochs are comparable.

BRIEF SUMMARY OF THE INVENTION

The present invention provides a solution to the shortcomings of the prior art. The present invention provides a method and system for utilizing empirical null hypothesis for a biological time series. Employing large-scale estimation methods facilitate the estimation of an empirical null density rather than using a theoretical density. The empirical null is considered more dispersed than the usual theoretical null distribution.

In one aspect of the present invention, a method is disclosed for determining if two epochs are comparable. The method comprises steps of selecting a first section of a biological time series. The method then establishing the first section as a baseline section. Further, selecting a second section for the measurement and determining the similarity of the second section to the baseline section using empirical null hypothesis.

In another aspect of the present invention a method is disclosed for determining if two sets of epochs are comparable. The method comprises the steps of selecting a first plurality of epochs of an EEG recording and establishing them as a baseline segment. The method further comprises generating a second plurality of epochs and calculating an amount that the second plurality of epochs is similar to the first plurality of epochs using large-scale testing to estimate an empirical null hypothesis for a subset of the epochs. The method also includes determining if the second plurality of epochs is from the EEG recording.

In yet another aspect of the present invention is an EEG system. The EEG system includes a processor communicably coupled to a computer readable medium. The computer readable medium includes instructions executable by the processor to: select a first epoch of an EEG recording; establish the first epoch as a baseline epoch; select a second epoch for measurement; and determine the similarity of the second epoch to the baseline epoch using empirical null hypothesis.

In an alternative embodiment, the empirical null measures a derived value from an EEG. The empirical null can measure an amount of power in a given frequency range of an EEG.

The result is a Z-score expressing the difference from a baseline that can then be displayed in a time series to show how the derived value is varying from the baseline over time.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

The present invention provides a solution to the shortcomings of the prior art. The present invention provides a method and a system for utilizing empirical null hypothesis for a biological time series. More specifically, the present invention provides a method and a system for utilizing empirical null hypothesis for raw score generated by the artificial neural networks.

Empirical Hypothesis refers to the use of working hypothesis that can be tested using observation and experiment, in other words this hypothesis is based on evidence. Empirical data is produced by experiment and observation. Null Hypothesis (denoted by $H_0$) exists when a researcher believes there is no relationship between the two variables, or there is a lack of information to state a scientific hypothesis. According to null hypothesis there is no significant difference between the specified populations, any observed difference being due to sampling or experimental error.

Empirical Null Hypothesis is generally assumed to be true until evidence indicates otherwise. A null hypothesis is rejected if the observed data are significantly unlikely to have occurred if the null hypothesis were true. In this case the null hypothesis is rejected and an alternative hypothesis is accepted in its place. If the data are consistent with the null hypothesis, then the null hypothesis is not rejected.

Empirical Null Hypothesis is explained as a way of example in the description provided below.

Hypothesis testing begins with a collection of null hypotheses $$H1, H2, \ldots HN$$

corresponding test statistics, possibly not independent, $$Y1, Y2, \ldots YN$$

and their p-values, P1, P2, ..., PN, with Pi measuring how strongly yi, the observed value of Yi, contradicts Hi, for instance Pi=prob Hi {|Yi|>|yi|}. "Large-scale" means that N is a large number, at least greater than 100.

It is convenient though not necessary to work with z-values instead of the Yi's or Pi's, $$zi = \Phi-1(Pi), i=1, 2, \ldots, N, (1.3)$$

Φ indicating the standard normal cumulative distribution function (cdf), Φ−1 (0.95)=1.645 etc. If Hi is exactly true then zi will have a standard normal distribution $$zi|Hi \sim N(0,1)$$

This is referred to herein as the theoretical null hypothesis.

Figure 5:
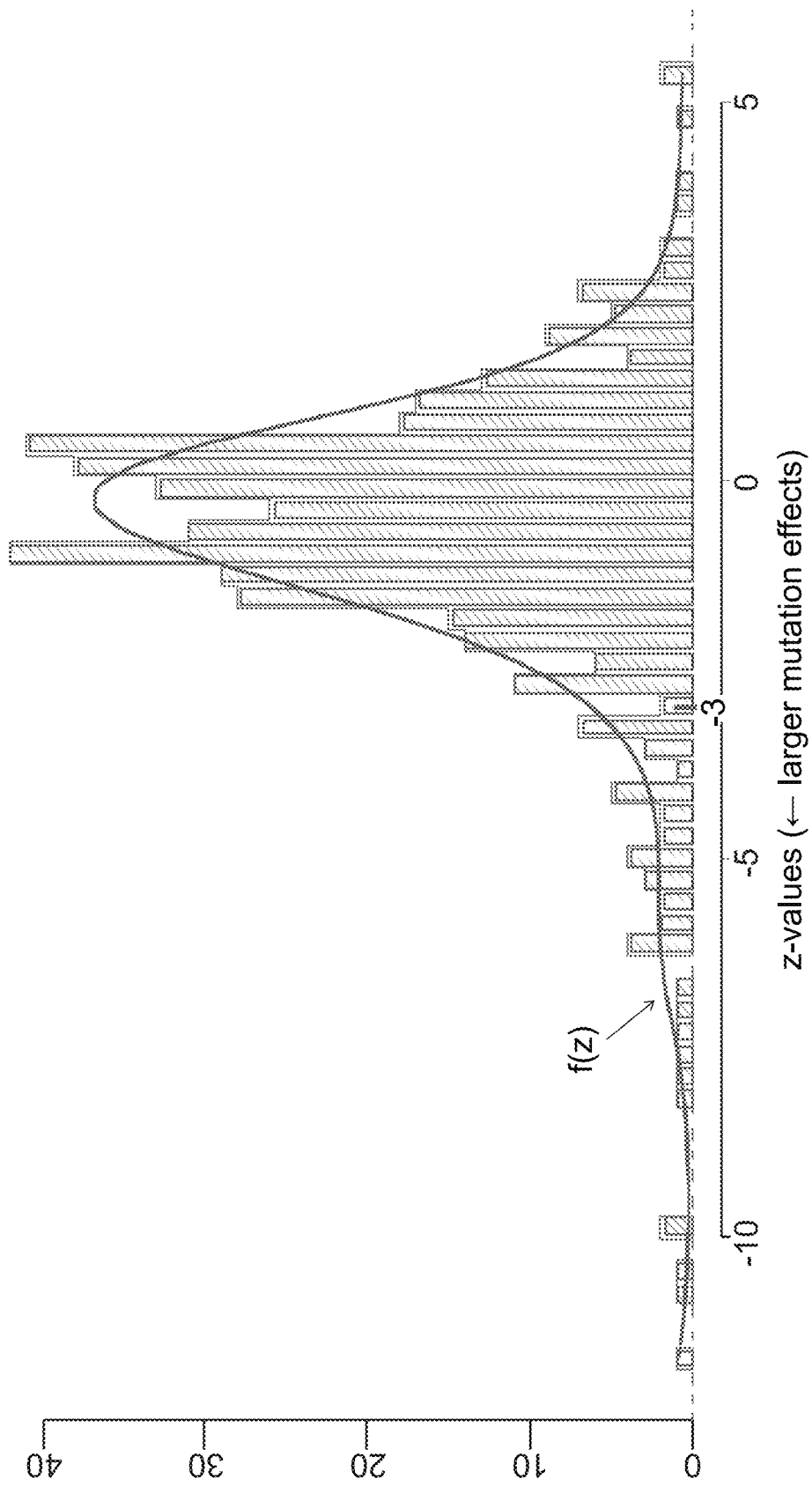
FIG. 5 is a graph illustrating the Empirical Null Hypothesis.

FIG. 5 is a graph describing the Empirical Null Hypothesis. FIG. 5 illustrates a histogram of the 444 z-values, with negative zi's indicating greater mutational effects. The smooth curve f(z) is a natural spline with seven degrees of freedom, fit to the histogram counts by Poisson regression. It emphasizes the central peak near z=0, presumably the large majority of uninteresting drug-site combinations that have negligible mutation effects. Near its center the peak is well-described by a normal density having mean −0.35 and standard deviation 1.20, which will be referred to as the empirical null hypothesis, $$zi|Hi \sim N(-0.35, 1.202)$$

Large-scale simultaneous hypothesis testing, where the number of cases exceeds, say 100, permits the empirical estimation of a null hypothesis distribution. The empirical null may be wider (more dispersed) than the theoretical null distribution that would ordinarily be used for a single hypothesis test. The choice between empirical and theoretical nulls can greatly influence which cases are identified as "Significant" or "Interesting," as opposed to "Null" or "Uninteresting," this being true no matter which simultaneous hypothesis testing method is used.

There are many possible reasons for over-dispersion of the empirical null distribution that would lead to the empirical null being preferred for simultaneous testing: Hidden correlations; A large proportion of genuine but uninterestingly small effects; Large-scale testing differs in scientific intent from an individual hypothesis test. The latter is most often designed to reject the null hypothesis with high probability. Large-scale testing is usually more of a screening operation, intended to identify a small percentage of interesting cases, assumed to be on the order of 10%.

After explaining the process of empirical null hypothesis in greater detail, now below provided description explains a solution for utilizing empirical null hypothesis for a biological time series. More specifically, the present invention provides a method and a system for utilizing empirical null hypothesis for raw score generated by the artificial neural networks.

Figure 1:
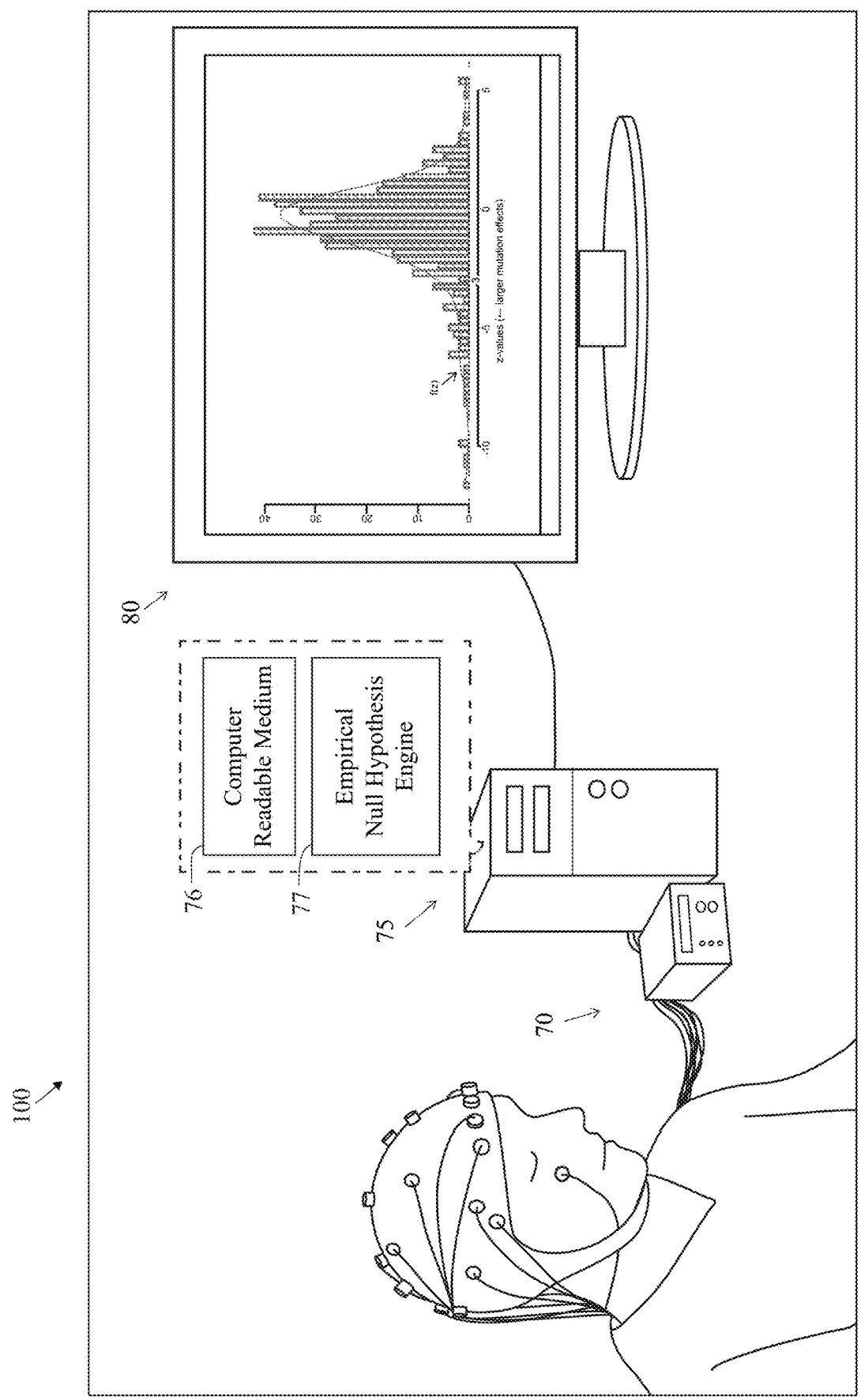
FIG. 1 is a system for utilizing empirical null hypothesis for a biological time series.

As shown in FIG. 1, a system 100 for utilizing empirical null hypothesis for a biological time series is generally designated. The system 100 preferably comprises a source 70, a processor 75, and a display 80. The source 70 generates digital input signals, which are received by the processor 75 connected to the source 70. The processor 75 comprises a computer readable medium 76 and an empirical null hypothesis engine 77. The computer readable medium includes instructions executable by the processor to: select a first epoch of an EEG recording; establish the first epoch as a baseline epoch; select a second epoch for measurement; and determine the similarity of the second epoch to the baseline epoch using empirical null hypothesis. The analyzed results are transmitted to the display device by the processor for the user.

In another aspect of the present invention, a method can be used for determining if two sets of epochs are comparable. The method comprises steps of selecting a first plurality of epochs of an EEG recording and establishing them as a baseline segment. The method further comprises generating a second plurality of epochs and calculating an amount that the second plurality of epochs is similar to the first plurality of epochs using large-scale testing to estimate an empirical null hypothesis for a subset of the epochs. The method also includes determining if the second plurality of epochs is from the EEG recording.

In yet another aspect of the present invention, disclosed is an EEG system. The EEG system includes a processor communicably coupled to a computer readable medium. The computer readable medium includes instructions executable by the processor to: select a first plurality of epochs of an EEG recording and establishing them as a baseline segment. The method further comprises generating a second plurality of epochs and calculating an amount that the second plurality of epochs is similar to the first plurality of epochs using large-scale testing to estimate an empirical null hypothesis for a subset of the epochs. In an example of a system 100, one hundred epochs of one second duration that were given a 30% probability score of a seizure, the system determines if thirty of those one hundred were actually a seizure. This occurs by calibrating fifty of the epochs to measure if seizures occurred in fifteen of those fifty, thereby selecting a first plurality of epochs of an EEG recording as a baseline segment. The calibration will provide a probability value, which will be validated against the remaining fifty epochs, thereby determining the second plurality of epochs is similar to the first plurality of epochs using large-scale testing to estimate an empirical null hypothesis. If fifteen of the remaining fifty evidence a seizure, then the probability value is validated.

A system for utilizing empirical null hypothesis for a biological time series is generally designated 100, and preferably comprises a source 70, a processor 75, and a display 80. At step 1, the source 70 generates digital input signals, which are received by the processor 75 at step 2. The processor being connected to the source 70. The processor 75 also comprises a computer readable medium 76. The computer readable medium includes instructions executable by the processor to: select a first epoch of an EEG recording; establish the first epoch as a baseline epoch; select a second epoch for measurement; and determine the similarity of the second epoch to the baseline epoch using empirical null hypothesis. The analyzed results are transmitted to the display device by the processor for the user.

The source 70 in FIG. 1 can be any device which provides data to the processor. The source can be an EEG machine which provides real-time biological signal detected from the neural activity of the brain of the person or can be a historical data stored in any datastore (e.g., databases, computer-readable storage media, directories, and the like). The datastore may comprise computer-readable storage media, such as hard disks, non-volatile solid-state storage devices, and the like. The datastores may provide data storage services, such as database storage services, directory services, and the like. The biological signal is any signal in living beings that can be continually measured and monitored. The term biological signal is often used to refer to bioelectrical signals or bio signals, but it may refer to both electrical and non-electrical signals. The usual understanding is to refer only to time-varying signals.

The system 100 comprises a processor 75. Without drifting away from the scope of the invention the processor can be a general purpose computer, computing device, microprocessor, microcontroller or any other computing device having a computer readable medium. The computer readable medium comprises a set of instructions for the processor to perform a certain method. The method will be described in greater detail below.

The processor transfers the computed results to a display device wherein the display device can be any electronic device having a display screen such as mobile phone, PDA, computer, LCDs, LEDs, TV screen etc. without limiting the scope of the invention.

The processor is configured to perform certain functions based on the certain set of instruction provided by the computer readable medium which will be explained below with the help of the examples.

Figure 2:
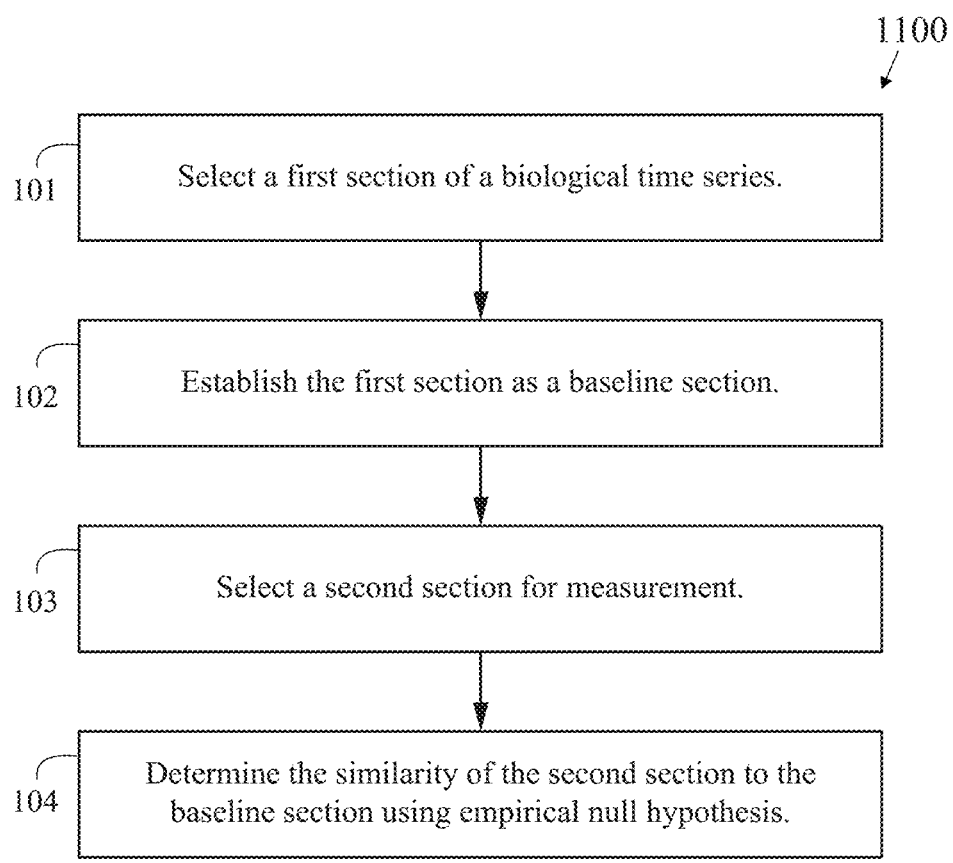
FIG. 2 is a flow chart of a method utilizing empirical null hypothesis for a biological time series.

FIG. 2 illustrates a flow chart for a preferred embodiment of the invention. FIG. 2 illustrates a flow chart of a method 1100 for determining similarity of the second section to a baseline section using empirical null hypothesis. At step 101, a first section of a biological time series is selected by a processor. The processor comprises a computer readable medium comprising a set of computer readable instruction to perform the method. At step 102, the selected first section of the biological time series is established as a baseline section. The step 102 leads to step 103 which selects a second section for measurement. At step 104, the second section is compared with the baseline section using empirical null hypothesis to determine the similarity with the baseline section. The biological time series can apply to EEGs, intracranial pressure, heart rate, or the like.

Figure 3:
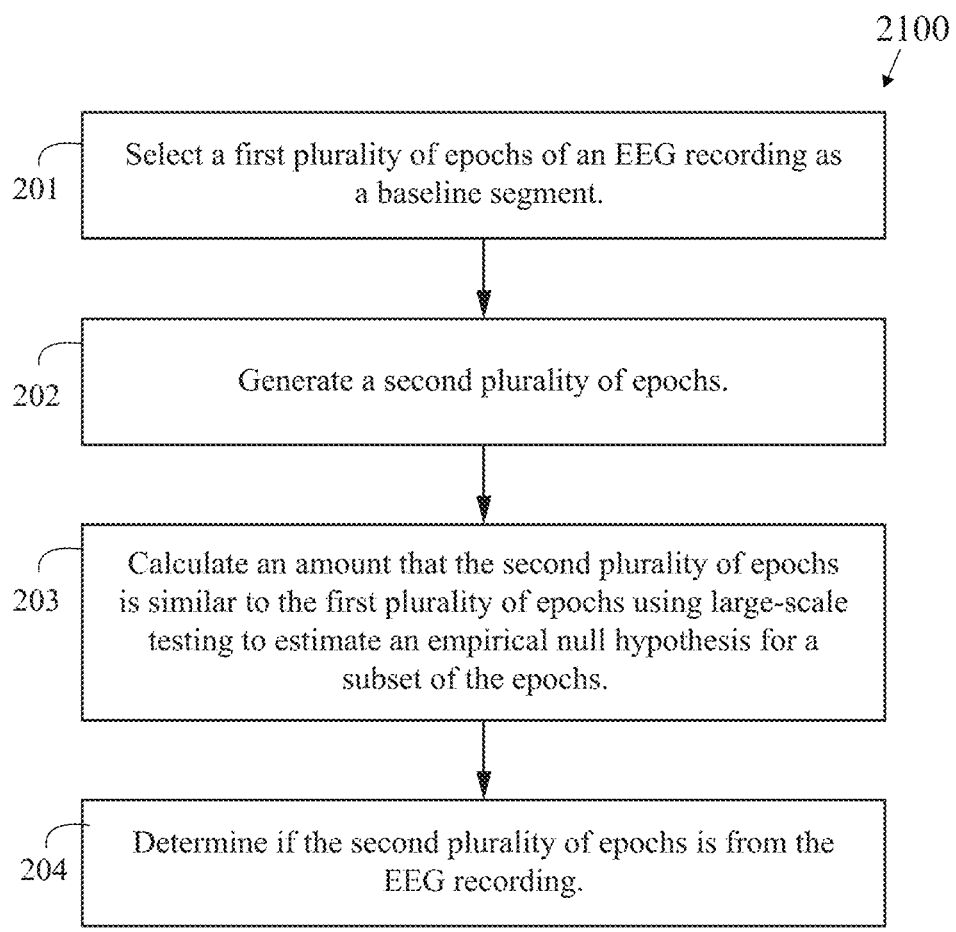
FIG. 3 is a flow chart of a method for utilizing empirical null hypothesis for a biological time series.
Figure 11:
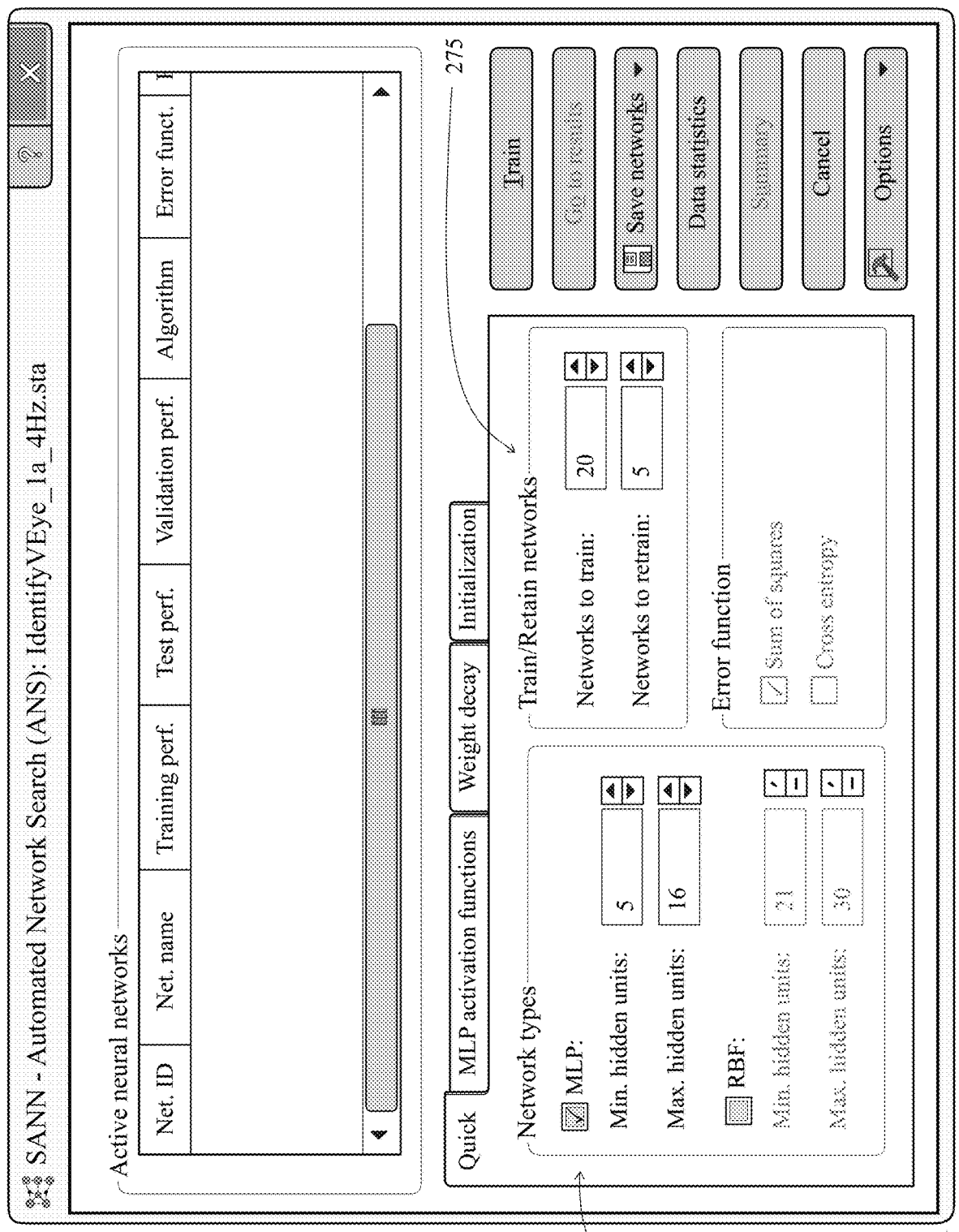
FIG. 11 illustrates an ANS window of an application, Statistical Automated Neural Networks.

FIG. 3 shows a flow chart for a method 2100 according to another embodiment of the invention. The FIG. 11 show a flow chart for the steps performed by a processor according to another embodiment of the invention. At step 201, a first plurality of epochs of an EEG recording are selected by the said processor. The processor comprises a computer readable medium comprising a set of computer readable instruction to perform the method. At step 201, the selected first plurality of epochs of an EEG recording are also established as a baseline segment. The step 201 leads to step 202 which generates a second plurality of epochs for measurement. At step 203, an amount is calculated that the second plurality of epochs which is similar to the first plurality of epochs using large-scale testing to estimate an empirical null hypothesis for a subset of the epochs. The method also includes determining if the second plurality of epochs is from the EEG recording.

Figure 4:
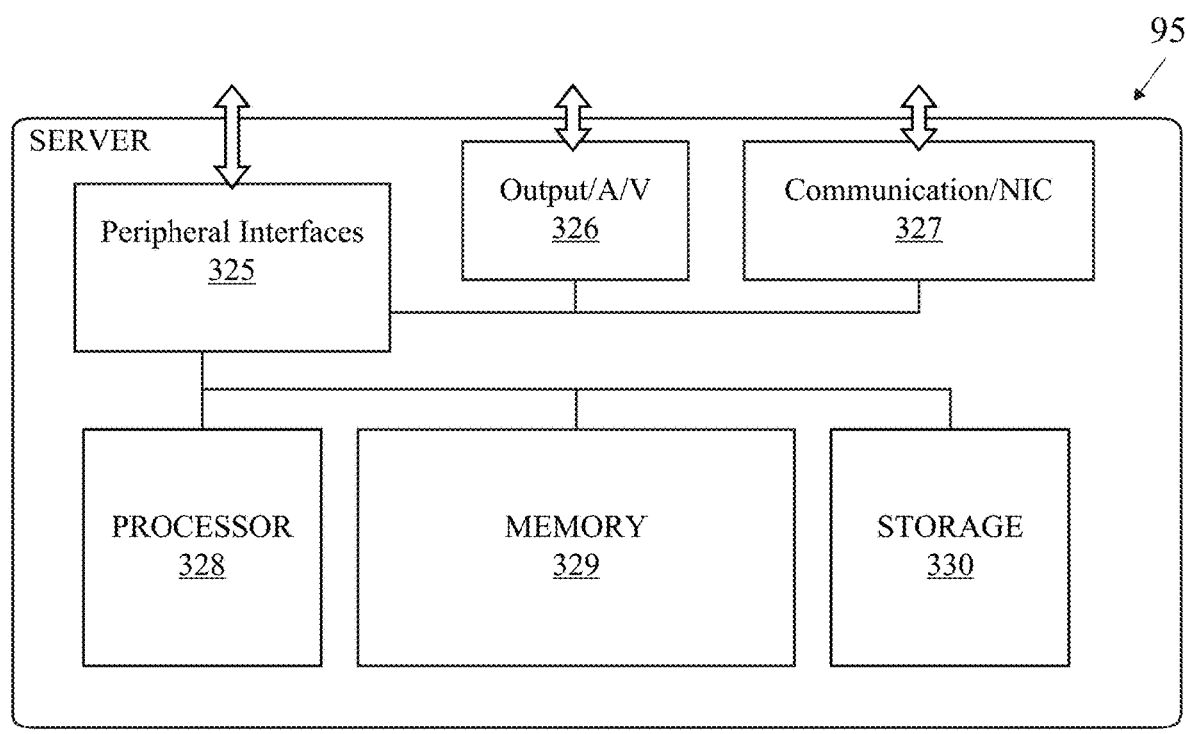
FIG. 4 is a block diagram of a computing device for EEG processing.

As shown in FIG. 4, the EEG machine component 95 utilized for determining if a second plurality of epochs is from the EEG recording preferably is a computer that includes peripheral interfaces 325, an output/A/V 326, a communication/NIC 327, a processor 328, a memory 329, and a storage 330. Those skilled in the pertinent art will recognize that the machine component 95 may include other components without departing from the scope and spirit of the present invention.

According to a novel aspect of the invention, a processor is configured to calibrate and validate the raw score processed through artifact reduction filters and neural network algorithms. The process of calibration and validation is performed based on the empirical null hypothesis. For example, taking one hundred epochs of one second duration that were given a 20% probability score of a seizure, the system determines if twenty of those one hundred were actually a seizure. This occurs by calibrating fifty of the epochs to measure if seizures occurred in ten of those fifty, thereby selecting a first section of the biological time series and establishing it as the baseline section. The calibration will provide a probability value, which will be validated against the remaining fifty epochs, which is a second section for measurement. The probability value is validated by determining the similarity of the second section to the baseline section using empirical null hypothesis. This also allows for training of a neural network to generate a validated probability value. This also allows for training of a neural network to generate a validated probability value.

In another embodiment of invention, with respect to system 100 of FIG. 1, a method can be used for determining if two sets of epochs are comparable. The method comprises steps of selecting a first plurality of epochs of an EEG recording and establishing them as a baseline segment. The method selects a first set of epochs and calibrates the probability value of the seizure. For example, taking one hundred epochs of one second duration that were given a 20% probability score of a seizure. The method further comprises generating/selecting a second plurality of epochs and calculating an amount that the second plurality of epochs is similar to the first plurality of epochs using large-scale testing to estimate an empirical null hypothesis for a subset of the epochs. The method checks for similarity between the first set of epochs and the second set of epochs. Based on the empirical Null hypothesis, if the probability value of a seizure of the second set of epochs is similar to the first set of selected epochs. Based on this calculation, it may determine if the second plurality of epochs is from the EEG recording.

Artificial neural networks (ANN) have been used to solve various tasks in numerous fields that are hard to solve using ordinary rule-based programming. An ANN can learn and adapt through learning algorithms. The types of ANNs and ANN architecture varies, mainly in the learning method.

The system for training a neural network for detecting artifacts in EEG recordings includes a plurality of electrodes for generating a plurality of EEG signals, a processor connected to the plurality of electrodes to generate an EEG recording from the plurality of EEG signals, and a display connected to the processor for displaying an EEG recording. Preferably, the processor is configured to train a neural network to learn to generate a plurality of sub-concept outputs from a first plurality of inputs.

In classification, the task is to a classify a variable $y=x_0$ called class variable or output given a set of variables $x=x_1 \ldots x_n$, called attribute variables or input. A classifier $h:x \rightarrow y$ is a function that maps an instance of x to a value of y. The classifier is learned from a dataset d consisting of samples over (x, y). The learning task consists of finding an appropriate Bayesian network given a data set d over U. Let $U=\{x_1, \ldots, x_n\}$, $n \geq 1$ be a set of variables.

Figure 12:
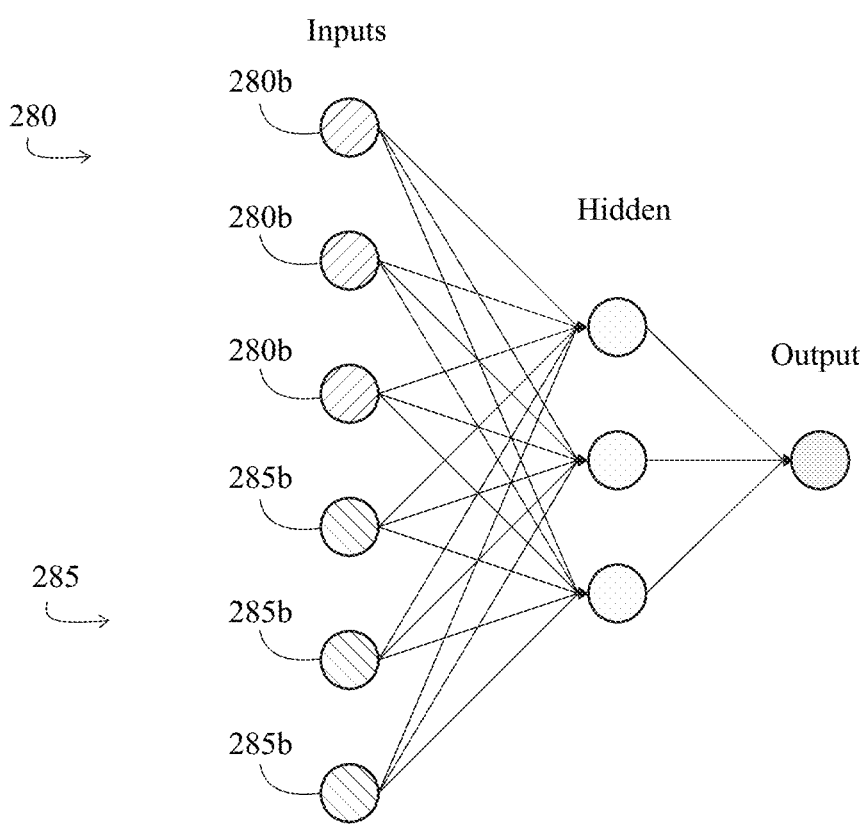
FIG. 12 is a block diagram of an MPL architecture.

FIG. 12 is a block diagram of an MPL architecture with inputs 280 and 285. A perceptron models a biological neuron as a mathematical function, $$y = \sum_{j=1}^{d} w_j x_j + w_0$$

where the weighted sum, y, of the input values, $x_j \in \mathcal{R}$, $j=1, \ldots, d$, are calculated. The weights are $w_j \in \mathcal{R}$.

The following is a Perceptron Training Algorithm for training a MLP with K outputs.

```
For i = 1,..., K
    For j = 0,..., d
        w_{ij} ← rand(-0.01,0.01)
Repeat
    For all (x^t, r^t) ∈ χ in random order
        For i= 1,..., K
            o_i ← 0
            For j = 0,..., d
                o_i ← o_i + w_{ij} x^t_j
        For i = 1,..., K
            y_i ← exp(o_i) / Σ_k exp(o_k)  For i = 1,..., K
                For j = 0,..., d
                    w_{ij} ← w_{ij} + η (r^t_i - y_i) x^t_j
Until convergence
```

Where η is the learning factor.

The following is a Backpropagation Algorithm for training a MLP with K outputs.

```
Initialize all v_{i h} and w_{hj} to rand(-0.01,0.01) Repeat
For all (x^t, r^t) ∈ χ in random order  For h = 1,..., H
    z_h ← sigmoid(w^T_h x^t)
    For i = 1,..., K
        y_i = v^T_i z
    For i = 1,..., K
        Δ v_i = η (r^t_i - y^t_i) z
    For h = 1,..., H
```

-continued

```
        Δ w_h = η ( Σ_i (r^t_i - y^t_i) v_{i h}) z_h (1 - z_h) x^t
    For i= 1,..., K
        v_i ← v_i + Δ v_i
    For h = 1,..., H
        w_h ← w_h + Δ w_h
until convergence.
```

Figure 6:
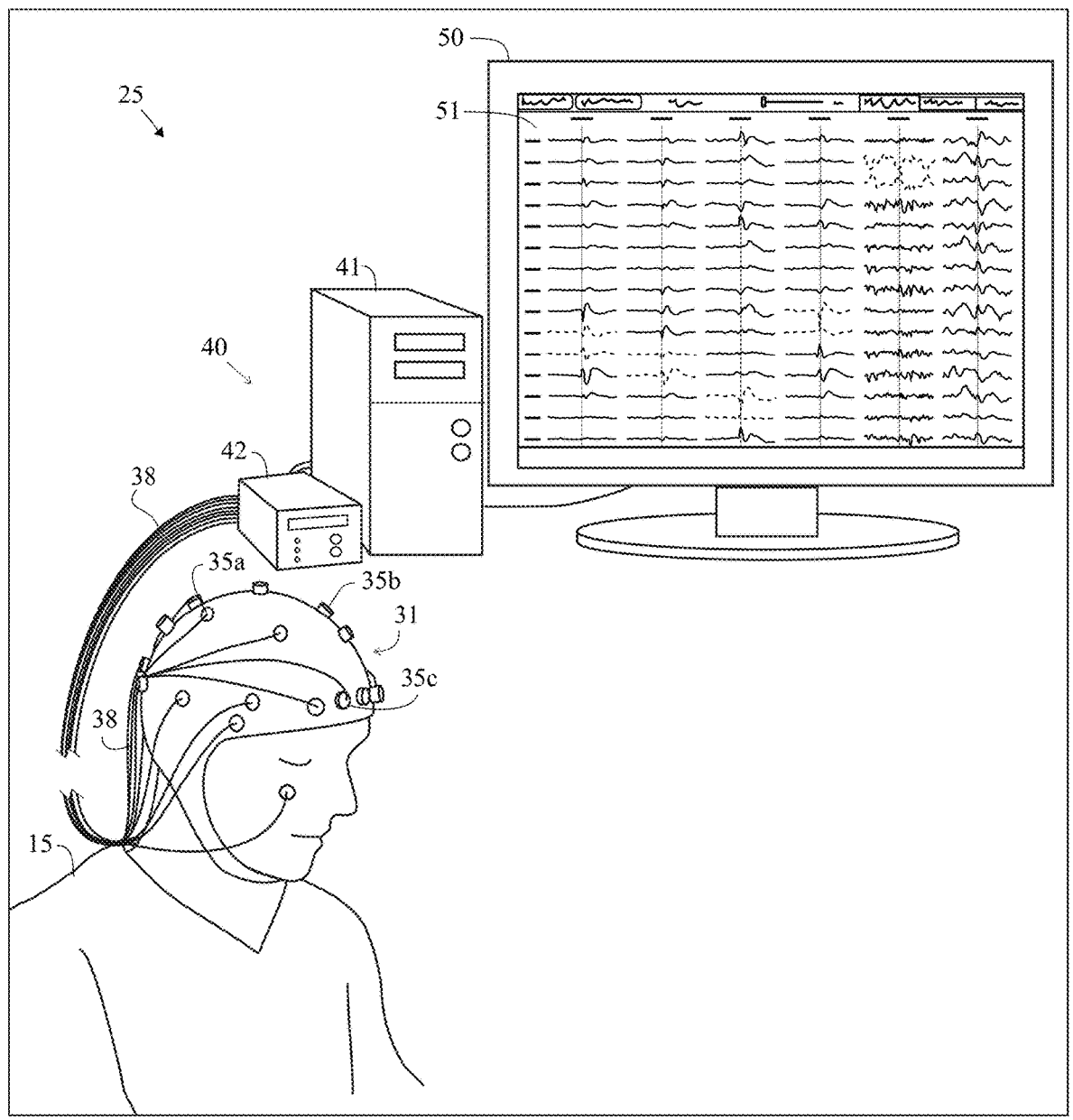
FIG. 6 is an illustration of an EEG system used on a patient.

FIG. 6 illustrates a system 25 for a user interface for automated artifact filtering for an EEG in which calculating an amount that a second plurality of epochs is similar to the first plurality of epochs using large-scale testing to estimate an empirical null hypothesis for a subset of the epochs in order to determine if the second plurality of epochs is from the EEG recording. A patient 15 wears an electrode cap 31, consisting of a plurality of electrodes 35a-35c, attached to the patient's head with wires 38 from the electrodes 35 connected to an EEG machine component 40 which consists of an amplifier 42 for amplifying the signal to a computer 41 with a processor, which is used to analyze the signals from the electrodes 35 and create an EEG recording 51, which can be viewed on a display 50. A button on computer 41, either through a keyboard or touchscreen button on display 50 allows for the application of a plurality of filters to remove the plurality of artifacts from the EEG and generate a clean EEG. A more thorough description of an electrode utilized with the present invention is detailed in Wilson et al., U.S. Pat. No. 8,112,141 for a Method And Device For Quick Press On EEG Electrode, which is hereby incorporated by reference in its entirety. The EEG is optimized for automated artifact filtering. The EEG recordings are then processed using neural network algorithms to generate a processed EEG recording, a raw score. The processor 41 is also configured to calibrate the raw score to generate a probability value that an event has occurred and then to generate a display of the probability value versus time. Further, the processor 41 is configured to validate the probability value. The processor is also connected to the display for displaying a final output.

The electrode 35a-35c may comprise a thin metal, such as a moderately electrically conductive alloy. In one embodiment, the electrode 35a-35c comprises a nitinol or other suitable shape memory material, metal or alloy. An electrode comprising one or more of these materials, metals or alloys may be bendable or deformable but may subsequently move towards its initial shape. For example, legs of an electrode comprising a shape memory metal may be configured to bend upon application of a force (e.g., a force applied by a human or machine prior to insertion of the electrode into a patient's skin) and to return towards an initial configuration upon release of said force (e.g., after the electrode has been inserted into the patient's skin). The legs may be bent away from the plane of an electrode body prior to insertion into a patient and may return towards this plane, such that the legs lie substantially parallel under a patient's skin after insertion, securing the position and insertion of the electrode.

In another embodiment, the electrode 35a-35c comprises stainless steel. The legs of the steel electrode 35a-35c are bent at an angle (e.g., about 25, 30, 40, 45 or 50 degrees) and pushed into the skin with enough force to affix the electrodes 35a-35c. In other embodiments, the electrode may be formed of any suitable conductive material, or combination of materials, with at least a portion of the electrode being formed of a conductive material. For example, other embodiments may comprise a nonconductive material with a conductive outer material.

The EEG is optimized for automated artifact filtering. The EEG recordings are then processed using neural network algorithms to generate a processed EEG recording which is analyzed for display.

An additional description of analyzing EEG recordings is set forth in Wilson et al., U.S. patent application Ser. No. 13/620,855, filed on Sep. 15, 2012, for a *Method And System For Analyzing An EEG Recording*, which is hereby incorporated by reference in its entirety.

Figure 7:
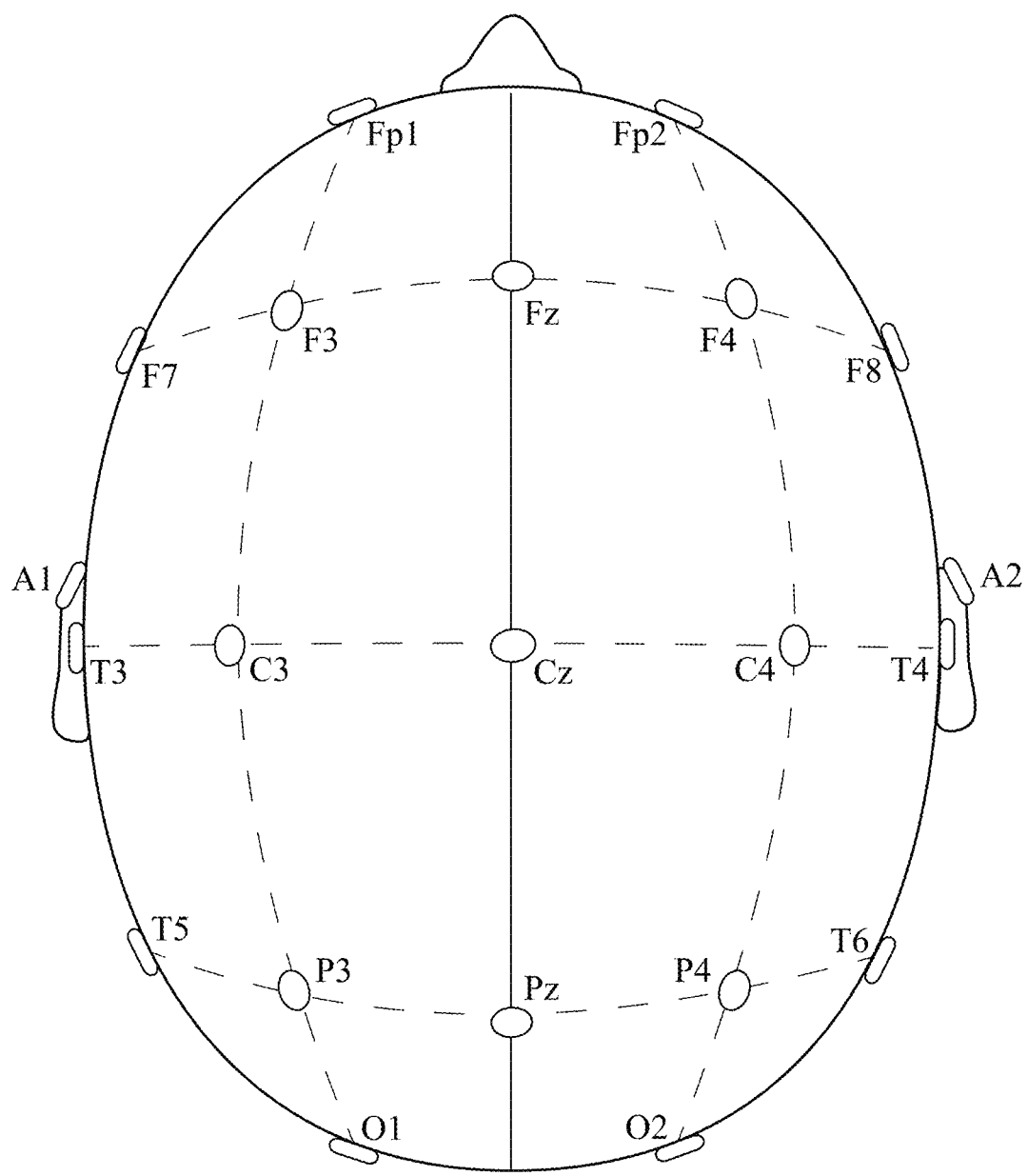
FIG. 7 is a map representing the international 10-20 electrode system for electrode placement for an EEG.
Figure 8:
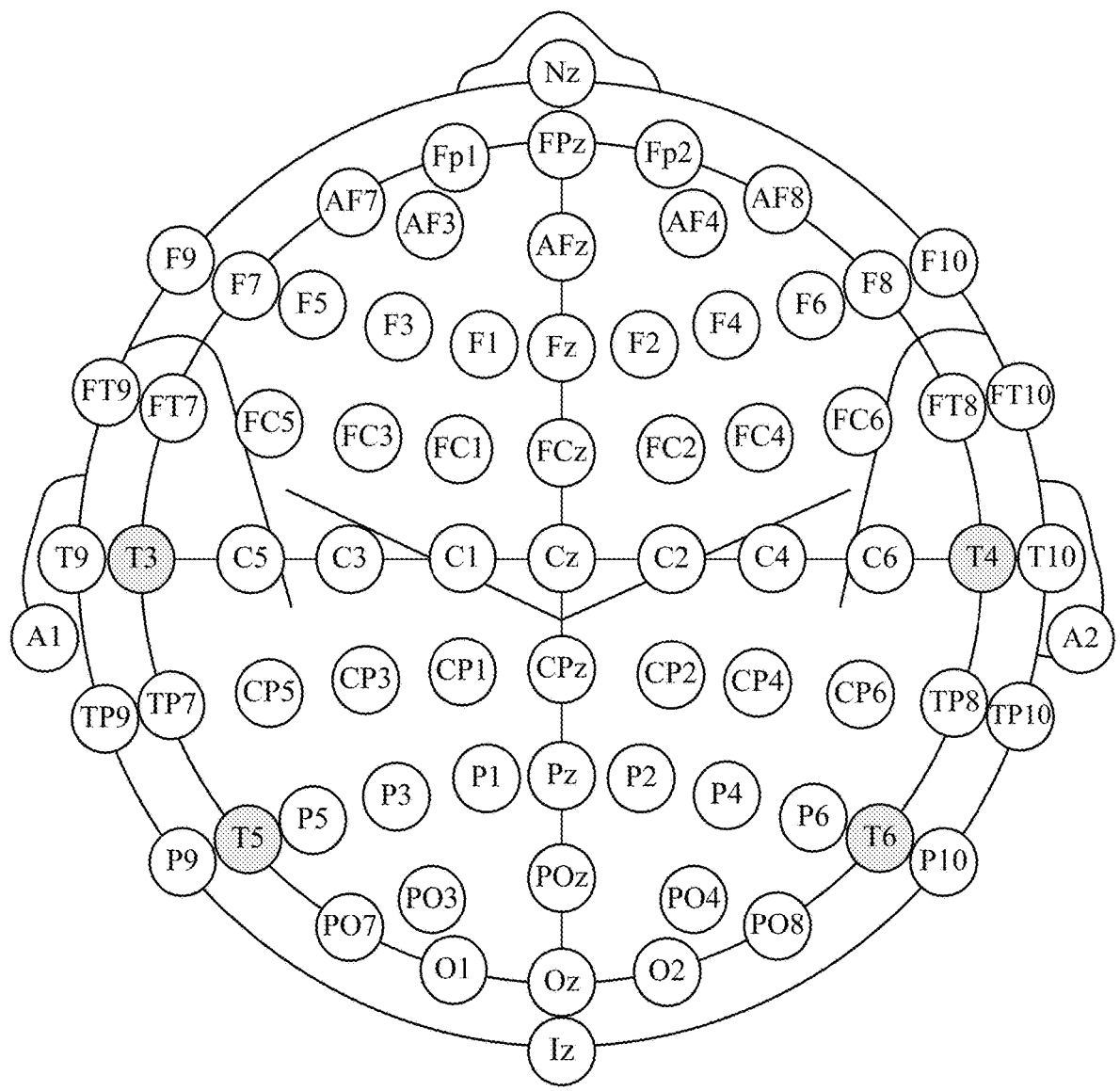
FIG. 8 is a detailed map representing the intermediate 10% electrode positions, as standardized by the American Electroencephalographic Society, for electrode placement for an EEG.

A patient has a plurality of electrodes attached to the patient's head with wires from the electrodes connected to an amplifier for amplifying the signal to a processor, which is used to analyze the signals from the electrodes and create an EEG recording. The brain produces different signals at different points on a patient's head. Multiple electrodes are positioned on a patient's head. The CZ site is in the center. The number of electrodes determines the number of channels for an EEG. A greater number of channels produce a more detailed representation of a patient's brain activity. Preferably, each amplifier 42 of an EEG machine component 40 corresponds to two electrodes 35 attached to a head of the patient 15. The output from an EEG machine component 40 is the difference in electrical activity detected by the two electrodes. The placement of each electrode is critical for an EEG report since the closer the electrode pairs are to each other, the less difference in the brainwaves that are recorded by the EEG machine component 40. FIG. 7 is a map representing the international 10-20 electrode system for electrode placement for an EEG. The term "electrode positioning" (10/20 system) refers to the standardized placement of scalp electrodes for a classical EEG recording. The essence of this system is the distance in percentages of the 10/20 range between Nasion-Inion and fixed points. These points are marked as the Frontal pole (Fp), Central (C), Parietal (P), occipital (O), and Temporal (T). The midline electrodes are marked with a subscript z, which stands for zero. The odd numbers are used as subscript for points over the left hemisphere, and even numbers over the right. FIG. 8 is a detailed map representing the intermediate 10% electrode positions, as standardized by the American Electroencephalographic Society, for electrode placement for an EEG. A more thorough description of an electrode utilized with the present invention is detailed in Wilson et al., U.S. Pat. No. 8,112,141 for a Method And Device For Quick Press On EEG Electrode, which is hereby incorporated by reference in its entirety.

Algorithms for removing artifact from EEG typically use Blind Source Separation (BSS) algorithms like CCA (canonical correlation analysis) and ICA (Independent Component Analysis) to transform the signals from a set of channels into a set of component waves or "sources."

In one example an algorithm called BSS-CCA is used to remove the effects of muscle activity from the EEG. Using the algorithm on the recorded montage will frequently not produce optimal results. In this case it is generally optimal to use a montage where the reference electrode is one of the vertex electrodes such as CZ in the international 10-20 standard. In this algorithm the recorded montage would first be transformed into a CZ reference montage prior to artifact removal. In the event that the signal at CZ indicates that it is not the best choice then the algorithm would go down a list of possible reference electrodes in order to find one that is suitable.

In one example for an eye blink removal, an epoch is first separated into sources using BSS (blind source separation). Each source is then reconstituted to the recorded montage and then to a CZ reference montage that is considered optimal for recognizing the eye blink type artifact. The channels of the CZ reference montage are examined by a neural network to determine if it is likely to be any eye blink. If it is, then this particular source is removed and the algorithm moves on to the next source. However, if there was an issue with the CZ electrode, then a different reference electrode would be selected for the source.

Figure 9:
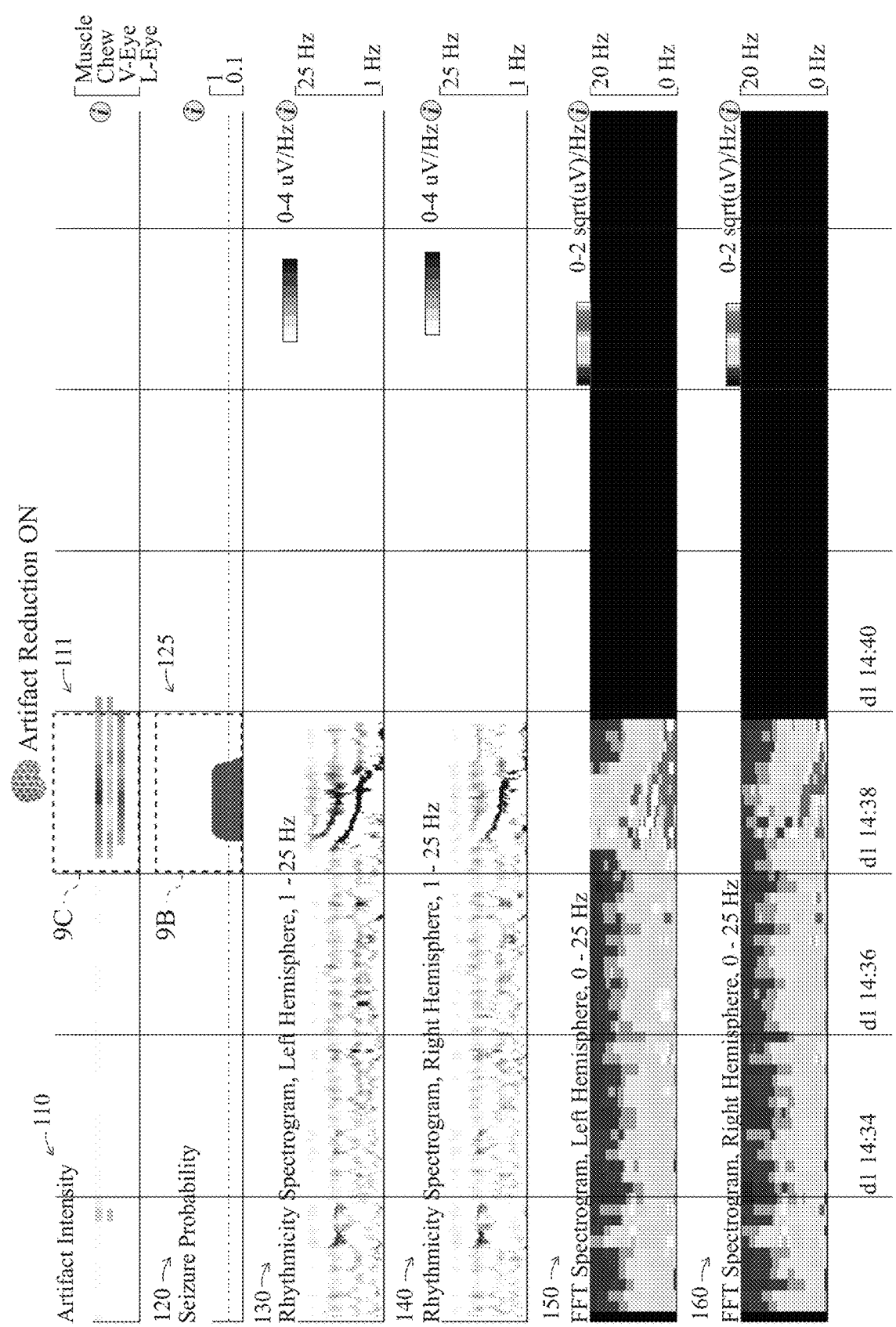
FIG. 9 is a graphical display of the amount of artifact present in an EEG recording.

FIGS. 9, 9A, 9B and 9C illustrate a graphical display of the amount of artifact present in an EEG recording in which calculating an amount that a second plurality of epochs is similar to the first plurality of epochs using large-scale testing to estimate an empirical null hypothesis for a subset of the epochs in order to determine if the second plurality of epochs is from the EEG recording. "Artifacts" are electrical signals detected along the scalp by an EEG, but that originate from non-cerebral origin. There are patient related artifacts (e.g., movement, sweating, ECG, eye movements) and technical artifacts (50/60 Hz artifact, cable movements, electrode paste-related). Persyst Artifact Reduction uses Blind Source Separation to separate the original EEG signal into its underlying components. It then uses a set of advanced neural networks to identify components arising from various types of artifact sources. In FIG. 9, an artifact intensity channel 110 is shown as a series of horizontal lines 111. The plurality of horizontal lines 111 shown comprises a horizontal line 112 for a muscle artifact, a horizontal line 113 for a chewing artifact, a horizontal line 114 for a vertical eye movement artifact, and a horizontal line 115 for a lateral eye movement artifact. Those skilled in the pertinent art will recognize that more or less horizontal lines may be used without departing from the scope and spirit of the present invention.

Figure 9A:
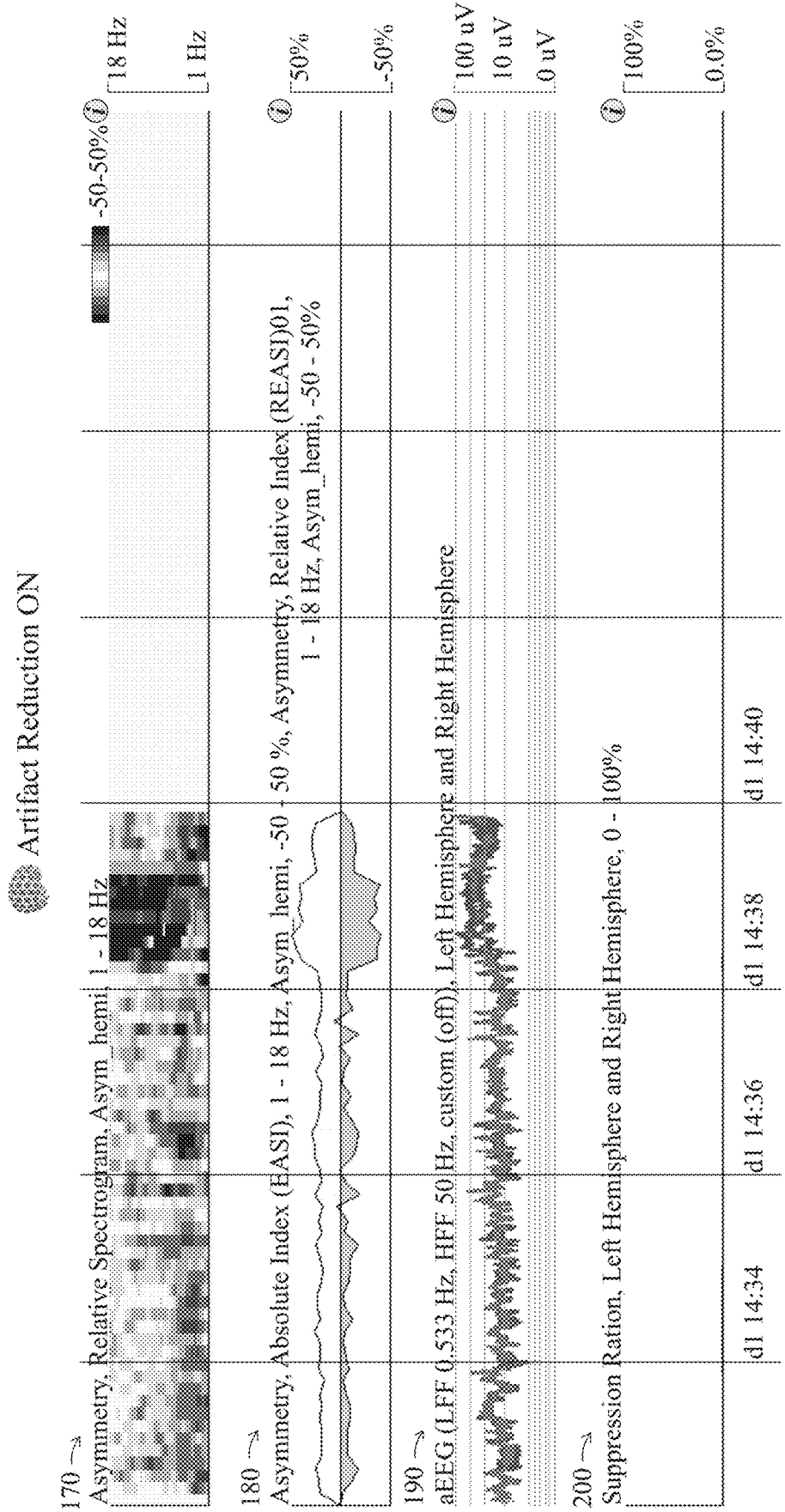
FIG. 9A is a graphical display of the amount of artifact present in an EEG recording.

Also shown in FIGS. 9 and 9A are a seizure probability channel 120, a rhythmicity spectrogram, left hemisphere channel 130, a rhythmicity spectrogram, right hemisphere channel 140, a FFT spectrogram left hemisphere channel 150, a FFT spectrogram right hemisphere channel 160, an asymmetry relative spectrogram channel 170, a asymmetry absolute index channel 180, an EEG channel 190, and a suppression ration, left hemisphere and right hemisphere channel 200.

Rhythmicity spectrograms allow one to see the evolution of seizures in a single image. The rhythmicity spectrogram measures the amount of rhythmicity which is present at each frequency in an EEG record. Rhythmicity spectrogram for left hemisphere 130 and right hemisphere 140 displays rhythmic components of different frequencies, darker colors being more rhythmic. Seizures are detected as a sudden increase in rhythmicity of delta and theta frequencies. The Rhythmicity Spectrogram measures the amount of rhythmicity present in each frequency band in the record. Rhythmicity Spectrograms, shows the evolution of seizures in a single image.

The seizure probability trend shows a calculated probability of seizure activity over time. The seizure probability trend shows the duration of detected seizures, and also suggests areas of the record that may fall below the seizure detection cut-off, but are still of interest for review. The seizure probability trend when displayed along with other trends, provides a comprehensive view of quantitative changes in an EEG. The seizure probability trend is determined by the seizure detection algorithm as indicated by bars 125.

FFT spectrogram for left hemisphere 150 and right hemisphere 160 shows powers of different frequencies in same/different colors. During seizures there is a flame shaped increase in the delta power. The increase in bright color over both hemispheres represents an increase in power at higher frequencies.

Figure 9B:
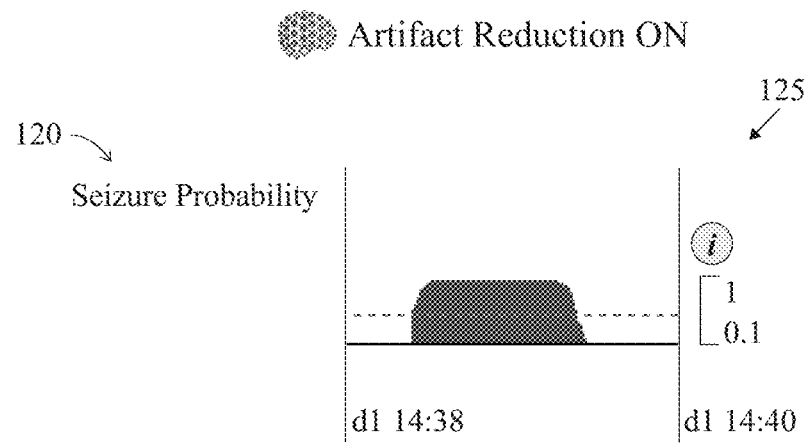
FIG. 9B is an enlarged and isolated view of a box 1B of a seizure probability channel of FIG. 9.

FIG. 9B shows the seizure being detected 125 in the seizure probability channel 120. The seizure probability trend shows a calculated probability of seizures over time, shows the duration of detected seizures, and also suggests areas of the record that may fall below the seizure detection cut-off, but are still of interest for review.

Figure 9C:
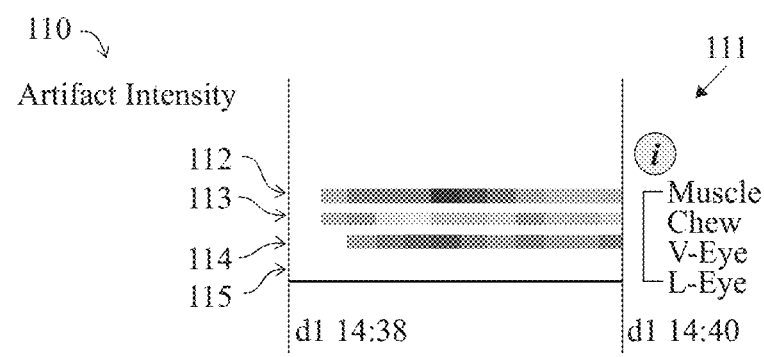
FIG. 9C is an enlarged and isolated view of horizontal lines of the artifact intensity channel of FIG. 9.

FIG. 9C shows an artifact intensity channel 110 as a series of horizontal lines 111. The plurality of horizontal lines 111 shown comprises a horizontal line 112 for a muscle artifact, a horizontal line 113 for a chewing artifact, a horizontal line 114 for a vertical eye movement artifact, and a horizontal line 115 for a lateral eye movement artifact. Those skilled in the pertinent art will recognize that more or less horizontal lines may be used without departing from the scope and spirit of the present invention.

Figure 10:
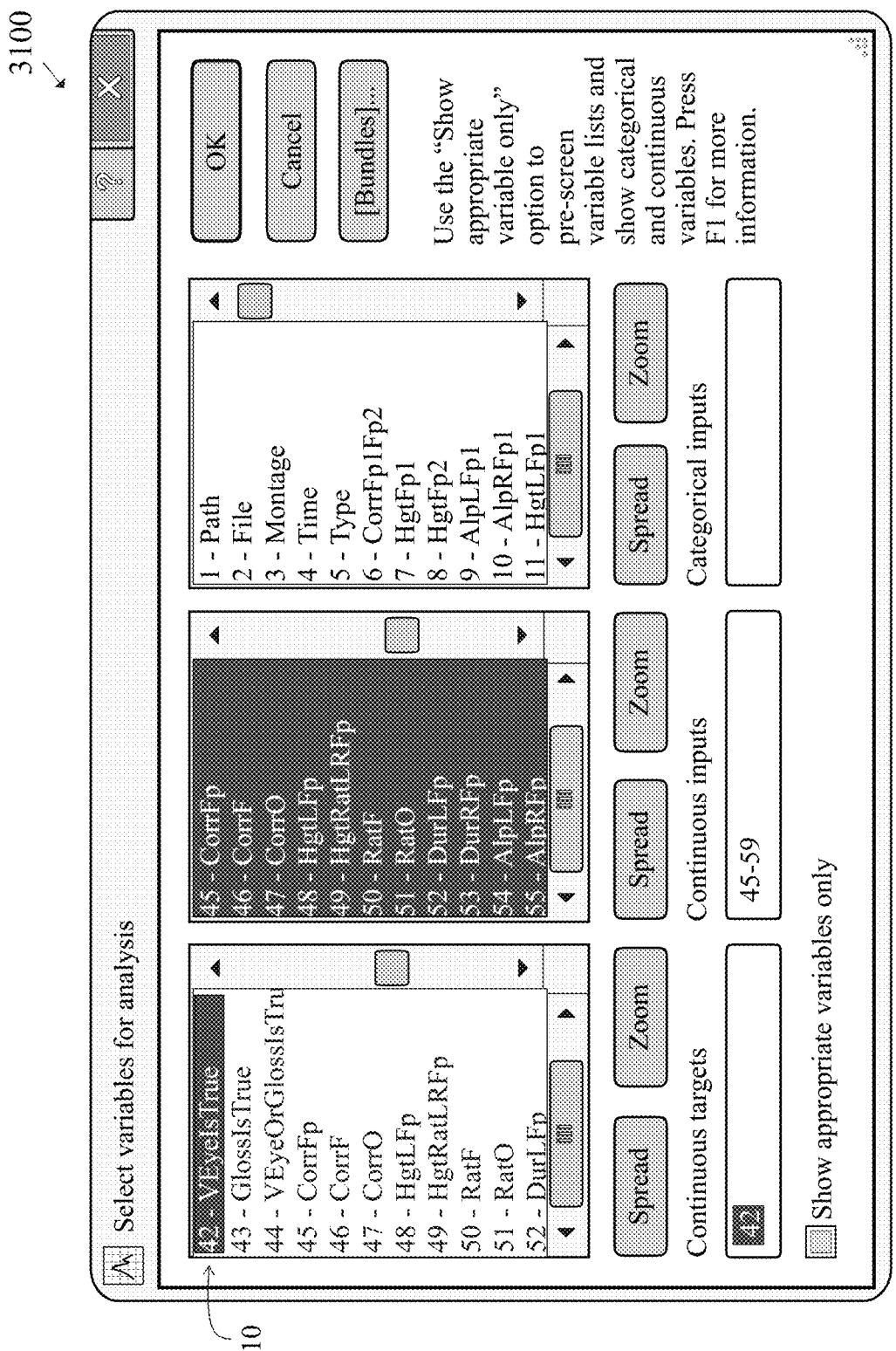
FIG. 10 illustrates a variables window of an application, Statistical Automated Neural Networks.

FIG. 10 illustrates a variables window of an application 3100, Statistical Automated Neural Networks.

FIG. 11 illustrates an ANS window 1150 of an application, Statistical Automated Neural Networks. The window includes network type tabs 270 and train/retrain networks tab 275.

Figure 13:
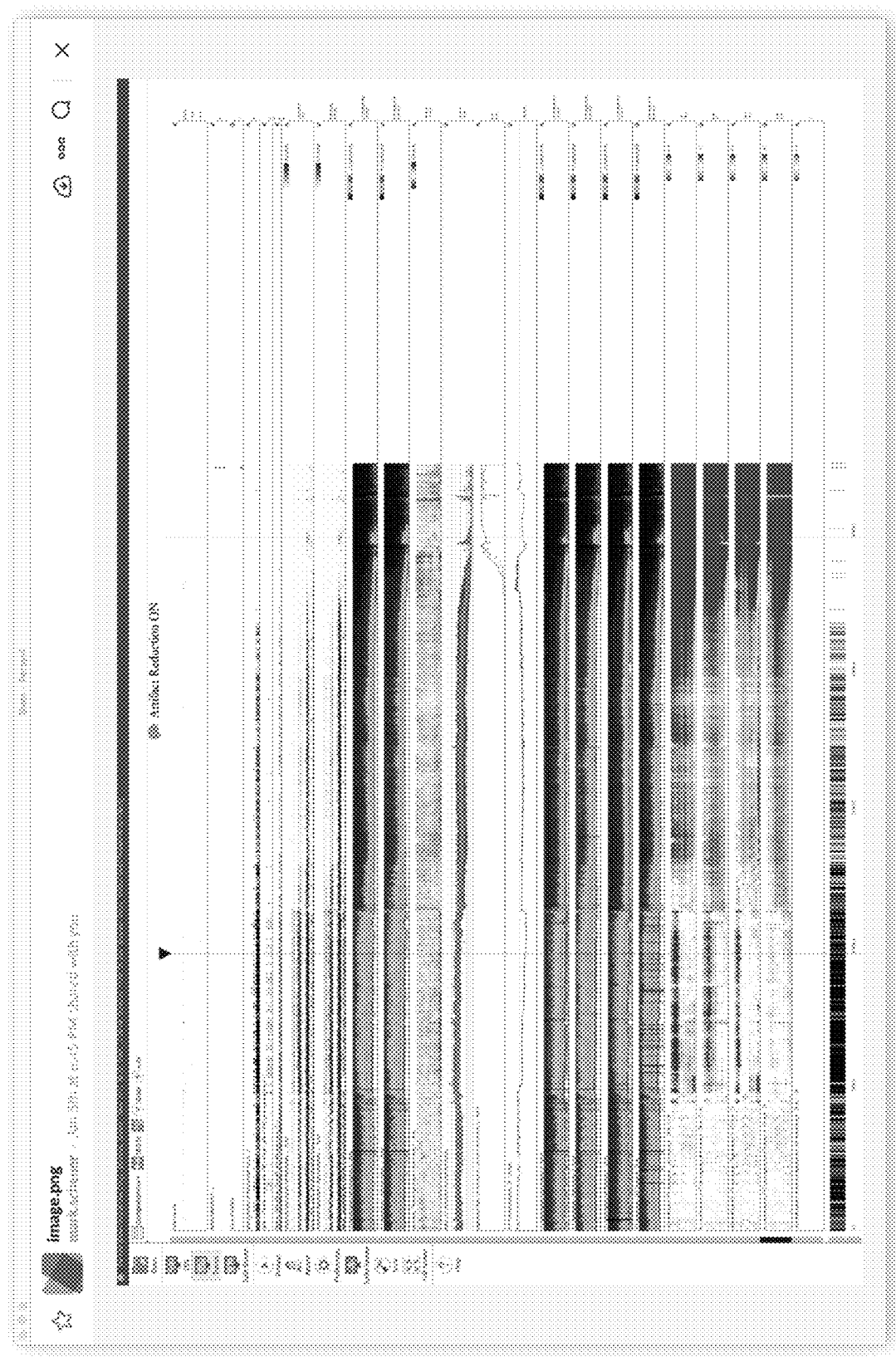
FIG. 13 is an image of EEG activity.

In a preferred embodiment, the empirical null measures a derived value from an EEG. The empirical null can measure an amount of power in a given frequency range of an EEG. The result is a Z-score expressing the difference from a baseline that can then be displayed in a time series to show how the derived value is varying from the baseline over time. The last four bands of FIG. 13 illustrate a z-score for derived values of an EEG including FFT at various times, frequencies, and sets of electrodes. The image can be displayed as an output of an EEG on the display device. The image is used to detect seizures. The image depicts the quantitative analysis of the epochs received from the EEG recording machine. The starting from the top of the image, the topmost trend shows artifact intensity. An artifact intensity channel shows a plurality of lines which suggests different types of artifacts such as a muscle artifact, a chewing artifact, a vertical eye movement artifact, a lateral eye movement artifact and the like. In other words, it shows how much artifact is present in the EEG at a specific point of time. The next trend is the seizure detection and seizure probability. The seizure probability trend shows a calculated probability of seizure activity over time. The seizure probability trend shows the duration of detected seizures, and also suggests areas of the record that may fall below the seizure detection cut-off, but are still of interest for review. They are blank in the image provided as there were no seizures present during the time period. After seizure detection and seizure probability, the next trend which follows is spike detection and spike rate. Further, there may be other trends displayed on the display screen. The examples for the other trends may be FFT trends, asymmetry spectrogram and the suppression ratio. The FFT trends are also called CSA trends.

The implementation of the empirical null hypothesis along with the neural networks improves the efficiency of the quantitative analyzed results displayed at the display screen. From the foregoing it is believed that those skilled in the pertinent art will recognize the meritorious advancement of this invention.

A more thorough description of an electrode utilized with the present invention is detailed in Wilson et al., U.S. Pat. No. 8,112,141 for a Method And Device For Quick Press On EEG Electrode, which is hereby incorporated by reference in its entirety. A more thorough description of EEG analysis utilized with the present invention is detailed in Wilson et al., U.S. patent application Ser. No. 13/620,855, filed on Sep. 15, 2012, for a Method And System For Analyzing An EEG Recording, which is hereby incorporated by reference in its entirety. A more thorough description of a user interface utilized with the present invention is detailed in Wilson et al., U.S. Pat. No. 9,055,927, for a User Interface For Artifact Removal In An EEG, which is hereby incorporated by reference in its entirety. An additional description of analyzing EEG recordings is set forth in Wilson et al., U.S. patent application Ser. No. 13/684,556, filed on Nov. 25, 2012, for a Method And System For Detecting And Removing EEG Artifacts, which is hereby incorporated by reference in its entirety. A more thorough description of displaying an EEG utilized with the present invention is detailed in Nierenberg et al., U.S. Pat. No. 8,666,484, for a Method And System For Displaying EEG Recordings, which is hereby incorporated by reference in its entirety. A more thorough description of displaying EEG recordings utilized with the present invention is detailed in Wilson et al., U.S. Pat. No. 9,232,922, for a User Interface For Artifact Removal In An EEG, which is hereby incorporated by reference in its entirety. An additional description of qEEG is set forth in Nierenberg et al., U.S. patent application Ser. No. 13/830,742, filed on Mar. 14, 2013, for a Method And System To Calculate qEEG, which is hereby incorporated by reference in its entirety. An additional description of using neural networks with the present invention is set forth in Wilson, U.S. patent application Ser. No. 14/078,497, filed on Nov. 12, 2013, for a Method And System Training A Neural Network, which is hereby incorporated by reference in its entirety. An additional description of using neural networks with the present invention is set forth in Nierenberg et al., U.S. patent application Ser. No. 14/222,655, filed on Jan. 20, 2014, for a System And Method For Generating A Probability Value For An Event, which is hereby incorporated by reference in its entirety. Wilson et al., U.S. patent application Ser. No. 15/131,216, filed on Apr. 18, 2016, is hereby incorporated by reference in its entirety.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention:

1. A method for determining if a first section of a biological time series is comparable to a second section of a biological time series, the method comprising:
  selecting, at a processor, a first section of a biological time series based on a plurality of digital signals generated from a source;
  establishing, at the processor, the first section as a baseline section, wherein the processor comprises a computer readable medium and an empirical null hypothesis engine that outputs an empirical null hypothesis;
  selecting, at the processor, a second section of the biological time series for measurement;

calibrating and validating a raw score processed through filters and neural network algorithms, wherein said calibrating and validating is based on the empirical null hypothesis, to provide a probability score of an event for the biological time series;

determining, at the processor, a similarity of the second section to the baseline section using the empirical null hypothesis in an empirical examination of data for a subset of the biological time series to validate the probability score of an event for the biological time series; and generating, at a processor, a Z-score expressing a difference from a baseline that is displayed in a time series on a display device to show how a derived value is varying from the baseline over time, wherein the display device is at least one of a mobile phone, a PDA, a computer, or a TV screen.

2. An EEG system, the EEG system comprising: a processor comprising a computer readable medium and an empirical null hypothesis engine that outputs an empirical null hypothesis, wherein the computer readable medium includes instructions executable by the processor to:

calibrate and validate a raw score processed through artifact reduction filters and neural network algorithms, wherein said calibrating and validating is based on the empirical null hypothesis, to provide a probability score of a seizure event;

select a first epoch of an EEG recording;

establish the first epoch as a baseline epoch;

select a second epoch of the EEG recording for measurement;

determine a similarity of the second epoch to the baseline epoch using the empirical null hypothesis in an empirical examination of data for a subset of the epochs to validate the probability score of a seizure event; and generate a Z-score expressing a difference from a baseline that is displayed in a time series on a display device to show how a derived value is varying from the baseline over time, wherein the display device is at least one of a mobile phone, a PDA, a computer, or a TV screen.

* * * * *